United States Patent
Glynn (10) Patent No.: US 9,272,036 B2
(45) Date of Patent: Mar. 1, 2016

(54) CARBON DIOXIDE, SALINE AND ADDITIONAL ACTIVE NASAL DELIVERY METHODS AND TREATMENTS

(75) Inventor: Kenneth P. Glynn, Flemington, NJ (US)

(73) Assignee: CLOVER HILL HEALTHCARE, INC., Flemington, NJ (US)

( * ) Notice: Subject to any disclaimer, the term of this patent is extended or adjusted under 35 U.S.C. 154(b) by 828 days.

(21) Appl. No.: 13/506,425

(22) Filed: Apr. 18, 2012

(65) Prior Publication Data

US 2013/0281917 A1  Oct. 24, 2013

(51) Int. Cl.
*A61K 45/06* (2006.01)
*A61K 33/00* (2006.01)
*A61M 31/00* (2006.01)
*A61M 11/02* (2006.01)

(52) U.S. Cl.
CPC ............... *A61K 45/06* (2013.01); *A61K 33/00* (2013.01); *A61M 11/02* (2013.01); *A61M 31/00* (2013.01); *A61M 2202/0225* (2013.01); *A61M 2205/3334* (2013.01); *A61M 2210/0618* (2013.01)

(58) Field of Classification Search
CPC ... A61K 45/06; A61K 33/00; A61K 2300/00; A61M 2210/0618; A61M 2202/0225; A61M 11/02; A61M 2205/3334; A61M 31/00
USPC ...................................... 128/203.14, 203.16
See application file for complete search history.

(56) References Cited

U.S. PATENT DOCUMENTS

| | | | |
|---|---|---|---|
| 7,827,986 B2 * | 11/2010 | Rasor et al. | 128/203.12 |
| 7,836,883 B2 | 11/2010 | Rasor et al. | |
| 7,845,348 B2 | 12/2010 | Rasor et al. | |
| 7,858,650 B2 | 12/2010 | Yamamoto et al. | |
| 7,959,597 B2 | 6/2011 | Baker et al. | |
| 8,007,842 B2 | 8/2011 | Rau | |
| 2004/0009126 A1 | 1/2004 | Pilkiewicz et al. | |
| 2006/0172017 A1 | 8/2006 | Rasor et al. | |
| 2008/0066739 A1 | 3/2008 | LeMahieu et al. | |
| 2008/0066741 A1 | 3/2008 | LeMahieu et al. | |
| 2008/0078382 A1 | 4/2008 | LeMahieu et al. | |
| 2008/0169047 A1 | 7/2008 | Connolly et al. | |
| 2012/0179122 A1 * | 7/2012 | Eilat et al. | 604/290 |

OTHER PUBLICATIONS

WO 2011/010310A1, Eilat et al., publication date: Jan. 27, 2011.*
Casale, et at, "Nasal Carbon Dioxide for the Symptomatic Treatment of Perennial Allergic Rhinitis" Date Published Oct. 2011, Ann Allergy Asthma Immunol., pp. 364-370.
Baroody et al., "The Effect of Intranasal Carbon Dioxide on the Acute Response to Nasal Challenge with Allergen" Date Published May-Jun. 2011, Allergy Asthma Proc., pp. 206-212.

(Continued)

*Primary Examiner* — Manuel Mendez
(74) *Attorney, Agent, or Firm* — Deirda M. Meagher, Esq.

(57) ABSTRACT

Methods for treating ailments in a patient in need thereof includes the step of directing a therapeutic, non-inhaled dosage to at least one nasal cavity of the patient through a flow regulating device while the patient refrains from inhaling. The dosage includes (a) a saline fluid (b) a gas containing carbon dioxide and (c) at least one additional active component, wherein the therapeutic, non-inhaled dosage is delivered at a flow rate from 1 cc/sec to 20 cc/sec for a duration of 2 to 30 seconds.

17 Claims, 5 Drawing Sheets

(56) References Cited

OTHER PUBLICATIONS

Pagani et al., "Carbon Dioxide-Enriched Water Inhalation in Patients With Allergic Rhinitis and its Relstionship with Nasal Fluid Cytokine/Chemokine Release" Date Published May 2011, Arch Med Res, pp. 329-333.

Casal, Romero, and Spierings, "Intranasal Noninhaled Carbon Dioxide for the Symptomatic Treatment of Seasonal Allergic Rhinitis" Date Published Jan. 2008, J Allergy Clin Immunol., pp. 105-109.

* cited by examiner

HEAD AILMENTS

- Rhinitis — 17
- Allergic Rhinitis — 19
- Conjunctivitis — 21
- The Common Cold — 23
- Sinusitis — 25
- Headache — 27

DURATION OF THERAPEUTIC NON-INHALED DOSAGE
(per nasal cavity)

- 2 to 30 seconds — 29
- 2 to 15 seconds — 31
- 5 to 10 seconds — 33

CARBON DIOXIDE, SALINE AND ADDITIONAL ACTIVE NASAL DELIVERY METHODS AND TREATMENTS

BACKGROUND OF INVENTION a. Field of Invention

The invention relates generally to healthcare, and specifically to the treatment of head ailments. More specifically, the present invention relates to intranasal delivery methods and treatments with carbon dioxide, saline and at least one additional active component.

b. Description of Related Art

The following patents and applications are representative of various types of nasal medicine delivery devices:

U.S. Pat. No. 8,007,842 B2 to Rau describes a composition for providing aromatherapy, and in particular, symptomatic relief of nasal and sinus congestion in unit dosage format. The composition includes a penetrating aromatic vapor whose release from a preparation of warm water is augmented by an effervescent component which reacts in the warm water to promote release of the aromatic fragrance, or sustained over time by tableting or gelatin encapsulation. As the fragrance is inhaled, symptomatic relief is obtained. The composition of matter may be rendered ingestible, so that the warm water containing the composition is consumed following inhalation. In preferred embodiments, the release of the penetrating aromatic fragrance persists over time.

U.S. Pat. No. 7,959,597 B2 to Baker et al. describes an irrigation and aspiration system. The system can be configured to aspirate and irrigate alone, sequentially or concurrently. The system can be configured to aspirate and irrigate the nasal cavity. The system can be manually controlled. The system can have removable and easily cleanable reservoirs for aspirant and irrigant.

U.S. Pat. No. 7,858,650 B2 to Yamamoto et al. describes a medicinal composition for inhalation containing a continuous-release type prodrug of an EP2 agonist which topically exhibits a prolonged bronchodilating and antiinflammatory effects. Namely, the medicinal composition for inhalation containing a continuous-release type prodrug of an EP2 agonist is useful as a safe preventive and/or a remedy for respiratory diseases (for example, asthma, pulmonary injury, pulmonary fibrosis, pulmonary emphysema, bronchitis, chronic obstructive pulmonary disease, adult respiratory distress syndrome, cystic fibrosis, pulmonary hypertension or the like) without causing any systemic effect such as lowering blood pressure. Thus, a safe and useful remedy for respiratory diseases is provided.

U.S. Pat. No. 7,845,348 B2 to Rasor et al. describes apparatus, methods, and kits for treating symptoms associated with common ailments, such as headaches, rhinitis, asthma, epilepsy, nervous disorders and the like. The apparatus comprises dispensers for carbon dioxide and other therapeutic gases. The methods comprise delivering small volumes of these gases to patients in a manner where the gas infuses into a body region in order to bathe the mucous membranes therein. It has been found that even very short exposure of patients to small volumes and high concentrations of such gases can provide significant relief from symptoms.

U.S. Pat. No. 7,836,883 B2 to Rasor et al. describes apparatus, methods, and kits for treating symptoms associated with common ailments, such as headaches, rhinitis, asthma, epilepsy, nervous disorders and the like. The apparatus comprises dispensers for carbon dioxide and other therapeutic gases. The methods comprise delivering small volumes of these gases to patients in a manner where the gas infuses into a body region in order to bathe the mucous membranes therein. It has been found that even very short exposure of patients to small volumes and high concentrations of such gases can provide significant relief from symptoms.

U.S. Pat. No. 7,827,986 B2 to Rasor et al. describes apparatus, methods, and kits for treating symptoms associated with common ailments, such as headaches, rhinitis, asthma, epilepsy, nervous disorders and the like. The apparatus comprises dispensers for carbon dioxide and other therapeutic gases. The methods comprise delivering small volumes of these gases to patients in a manner where the gas infuses into a body region in order to bathe the mucous membranes therein. It has been found that even very short exposure of patients to small volumes and high concentrations of such gases can provide significant relief from symptoms.

United States Patent Application No. 2008/0169047 A1 to Connolly et al. describes a hand-held, low-flow dispenser which comprises an enclosure holding a gas cartridge. A spring-biased needle is advanced to puncture a septum on the gas cartridge, and a separate spring-biased ball valve is used to turn the resulting gas flow off and on as well as to control the flow rate.

United States Patent Application No. 2008/0078382 A1 to LeMahieu et al. describes systems and methods for delivery of a drug to the respiratory system of a patient in a stream of purified air are provided. In particular, the drugs are delivered to the respiratory system of the patient at a positive air pressure relative to atmospheric pressure. With the systems and methods of the present disclosure, medication available in a variety of forms is introduced in a controlled fashion into the air stream in aerosol, nebulized, or vaporized form.

United States Patent Application No. 2008/0066741 A1 to LeMahieu et al. describes systems and methods for delivery of a drug to the respiratory system of a patient, where the drug is supplied in purified air at a positive pressure relative to atmospheric pressure. With the systems and methods of the present disclosure, medication available in a variety of forms is introduced in a controlled fashion into the purified air stream in aerosol, nebulized, or vaporized form.

United States Patent Application No. 2008/0066739 A1 to LeMahieu et al. describes systems and methods for delivery of a drug to the respiratory system of a patient where the drug is supplied at a positive pressure relative to atmospheric pressure. In particular, the drugs are delivered to the respiratory system of a patient who is capable of unassisted breathing. With the systems and methods of the present disclosure, medication available in a variety of forms is introduced in a controlled fashion into the air stream in aerosol, nebulized, or vaporized form.

United States Patent Application No. 2006/0172017 A1 to Rasor et al. describes an apparatus and methods to deliver vasoconstrictive agents simultaneously with capnic gases. The capnic gases can enhance the effectiveness of the vasoconstrictive agent, lower the dosage of drug or concentration of agent necessary to achieve a therapeutic result, or both. Exemplary capnic gases include carbon dioxide, nitric oxide, nitrous oxide, and dilute acid gases.

United States Patent Application No. 2004/0009126 A1 to Pilkiewicz et al. describes an inhalation system comprising an anti-infective agent in particle form, the anti-infective agent being directed toward prevention and treatment of intracellular infection, and an inhalation device, and a method of use of the system.

United States Patent Application No. 2002/0040205 A1 to Rasor et al. describes methods and devices for transcutaneous and transmucosal application of carbon dioxide in the form of gas and in the form of a capnic solution (such as carbonated water) for the relief of pain, including musculoskeletal disorders, neuralgias, rhinitis and other ailments. Gaseous carbon is applied to the skin for at least three minutes, and the capnic solution may be held on the skin for at least three minutes, which provides relief of symptoms. The capnic solution may be sprayed onto mucous membranes such as the nose for relief of symptoms such as allergic rhinitis.

Casale, et al., "Nasal Carbon Dioxide for the Symptomatic Treatment of Perennial Allergic Rhinitis," Ann Allergy Asthma Immunol., October 2011, pp. 364-370, examines the safety and efficacy of nasal carbon dioxide on the symptoms of perennial allergic rhinitis.

Baroody et al., "The Effect of Intranasal Carbon Dioxide on the Acute Response to Nasal Challenge with Allergen," Allergy Asthma Proc., May-June 2011, pp. 206-212 describes a study in which intranasal carbon dioxide (CO(2)) was shown to reduce symptoms of seasonal allergic rhinitis (SAR). This study was designed to evaluate the effect of CO(2) on nasal allergen challenge. We conducted a randomized, controlled, crossover trial in 12 subjects with SAR outside their pollen season. Thirty minutes after a 20-second exposure to CO(2) or no exposure, subjects underwent a unilateral, localized, nasal allergen challenge. Filter paper disks were placed on the nasal septum to deliver a sham challenge followed by 2 increasing doses of either grass or ragweed allergen. Secretions were collected from both sides of the septum to evaluate the nasonasal reflex and were assayed for histamine. Nasal and eye symptoms were recorded. The primary outcome measure was the contralateral, reflex, secretory response to allergen as measured by secretion weights. Secondary outcome measures included ipsilateral nasal secretion weights, nasal and eye symptoms, levels of histamine in nasal secretions, and eosinophils in nasal scrapings. Subjects reported a transient burning sensation during exposure to CO(2). Compared with no treatment, active treatment resulted in a significant reduction in sneezes ($p=0.05$), contralateral secretion weights ($p=0.04$), and bilateral runny nose symptoms ($p=0.01$). Ipsilateral secretion weights were numerically reduced. Histamine levels in ipsilateral nasal secretions increased significantly when the subjects received sham treatment but did not increase after pretreatment with CO(2). Treatment with nasal CO(2) resulted in partial reduction of the acute response to allergen challenge. Reflex responses were reduced, supporting an effect on neuronal mechanisms, which predict usefulness in the treatment of allergic rhinitis.

Pagani et al., "Carbon Dioxide-Enriched Water Inhalation in Patients With Allergic Rhinitis and its Relationship with Nasal Fluid Cytokine/Chemokine Release," Arch Med Res, May 2011, pp. 329-333 investigates a possible in vivo effect of carbon dioxide-enriched water inhalation in patients with allergic rhinitis.

Casale, Romero, and Spierings, "Intranasal Noninhaled Carbon Dioxide for the Symptomatic Treatment of Seasonal Allergic Rhinitis," J Allergy Clin Immunol., January 2008, pp. 105-109, studies whether noninhaled intranasal CO2 would be effective in the treatment of seasonal allergic rhinitis.

Notwithstanding the prior art, the present invention is neither taught nor rendered obvious thereby.

SUMMARY OF INVENTION

The present invention is directed to a method for treating ailments in a patient in need thereof. It includes the step of directing a therapeutic, non-inhaled dosage to at least one nasal cavity of the patient through a flow regulating device. The dosage includes; (a) a saline fluid, (b) a gas containing carbon dioxide and (c) at least one additional active component, wherein the therapeutic, non-inhaled dosage is delivered at a flow rate from 1 cc/sec to 20 cc/sec for a duration of 2 to 30 seconds. The invention includes the step of having the patient substantially refrain from inhaling while the fluid is being released.

In some preferred embodiments of the present invention method for treating ailments in a patient in need thereof, the head ailment is rhinitis.

In some preferred embodiments of the present invention method for treating ailments in a patient in need thereof, the head ailment is conjunctivitis.

In some preferred embodiments of the present invention method for treating ailments in a patient in need thereof, the head ailment is the common cold.

In some preferred embodiments of the present invention method for treating ailments in a patient in need thereof, the head ailment is sinusitis.

In some preferred embodiments of the present invention method for treating ailments in a patient in need thereof, the head ailment is a headache.

In some preferred embodiments of the present invention method for treating ailments in a patient in need thereof, the flow regulating device is a single dose dispenser with a pressure control valve for released flow regulation.

In some preferred embodiments of the present invention method for treating ailments in a patient in need thereof, the flow regulating device is a multiple dose dispenser with a pressure control valve for released flow regulation. In some of these preferred embodiments of the present invention method for treating ailments in a patient in need thereof, the multiple dose dispenser further includes a dosage amount control mechanism and activator to limit dosage release amount for each activation.

In some preferred embodiments of the present invention method for treating ailments in a patient in need thereof, the duration is 5 to 10 seconds per nasal cavity.

In some preferred embodiments of the present invention method for treating ailments in a patient in need thereof, the duration is 2 to 15 seconds per nasal cavity.

In some preferred embodiments of the present invention method for treating ailments in a patient in need thereof, the dose is repeated from 1 to 10 times.

In some preferred embodiments of the present invention method for treating ailments in a patient in need thereof, the method is for treating rhinitis and the rhinitis is allergic rhinitis.

In some preferred embodiments of the present invention method for treating ailments in a patient in need thereof, the flow rate is from 2 cc/sec to 10 cc/sec.

In some preferred embodiments of the present invention method for treating ailments in a patient in need thereof, the flow rate is from 1 cc/sec to 5 cc/sec.

In some preferred embodiments of the present invention method for treating ailments in a patient in need thereof, the flow rate is from 4 cc/sec to 5 cc/sec.

In some preferred embodiments of the present invention method for treating ailments in a patient in need thereof, the gas includes at least 50% carbon dioxide.

In some preferred embodiments of the present invention method for treating ailments in a patient in need thereof, the gas includes at least 70% carbon dioxide.

In some preferred embodiments of the present invention method for treating ailments in a patient in need thereof, the gas includes at least 95% carbon dioxide.

In some preferred embodiments of the present invention method for treating ailments in a patient in need thereof, the gas is substantially pure carbon dioxide.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings.

DETAILED DESCRIPTION OF THE EMBODIMENTS

"Saline" and "saline solution" as used herein means water containing salt. Saline solutions are used in a wide variety of medical applications. For example, "normal saline" is the commonly used term for a solution of 0.90% w/v of sodium chloride (NaCl). Normal saline is frequently used in intravenous drips for patients unable to take fluids orally to prevent dehydration. Normal saline is also used to flush wounds and skin abrasions. Another application of saline solution is as a rinse for contact lenses.

Saline solution also is frequently used in nasal washes to treat some of the symptoms of the common cold or other ailments adversely affecting the nasal cavities. By irrigating the nasal passages with saline, inflammation can be reduced. Also, more concentrated ("hypertonic") solutions of NaCl, can have therapeutic uses. For example, 7% NaCl/water solutions are considered mucoactive agents and as such are used to hydrate thick secretions (mucous) in order to make it easier to cough up and out (expectorate).

Another chemical substance useful in medical treatments is carbon dioxide. One example is the use of diluted carbon dioxide by inhalation for treating symptoms related to headaches, allergies, asthma, nervous disorders, and other common ailments, which was demonstrated in the 1940s and 1950s. Another example is the use of high-concentration, non-inhaled carbon dioxide, delivered to the nasal passages locally. This type of treatment may provide fast relief without the adverse side effects of systemic drugs that are inhaled, ingested, or injected.

By combining the beneficial therapeutic effects of saline treatment and carbon dioxide treatment, an improved therapy is created. In this way, the beneficial effects of the saline, such as reduced inflammation and expectoration of mucous, are combined with the beneficial effects of carbon dioxide therapy, such as relief from headaches, allergies, asthma, nervous disorders, and other common ailments. In addition, the saline reduces any slight burning that might otherwise be felt from the carbon dioxide. Further, the saline moisturizes the nasal cavities and acts as a base host for the carbon dioxide as it acts on the nasal cavity walls. (It is hypothesized that at least some of the carbon dioxide is adsorbed by the saline.) In this way, the benefits of saline treatment are supplemented by the benefits of carbon dioxide treatment, and the benefits of carbon dioxide treatment are supplemented by the benefits of saline treatment. This combination of utilizing the saline to perform at least moisturizing and other beneficial affects while carrying and enhancing the delivery of the carbon dioxide is an unexpected synergistic result thereof.

In addition to the benefits listed above, the present invention carbon dioxide and saline nasal delivery methods and treatments have other synergistic benefits that are not available from either saline treatment or carbon dioxide treatment alone. For example, the presence of dissolved carbon dioxide in the saline solution means that the solution will be carbonated; the effervescent effect of the carbon dioxide helps the saline solution to mix more energetically against the interior surface of the nasal cavity or cavities. This improved mixing allows the saline treatment to be more effective. Another potential advantage of combining carbon dioxide and saline treatments is that in some embodiments, with sufficient pressure and a proper nozzle, the carbon dioxide can act as a carrier gas for the saline, allowing the saline solution to be aerosolized.

To summarize the advantages and benefits of the present invention, the combination of controlled delivery carbon dioxide/saline/additional active component(s) provides the following: it cleanses the nasal cavity removing allergens and particulates that cause inflammation and congestion; its special formula shields nasal mucosa from viruses; it soothes and moisturizes irritated mucosa; its unique buffering system neutralizes inhaled irritants such as oxidative free radicals and endogenous cytotoxins which cause inflammation and damage to the sensitive mucosa and muco-cillary hairs in the nasal cavity; it enhances mucous clearance and flow by reducing mucus viscosity; its superior safety profile gives it broader application than corticosteroids and decongestants and can be used safely in children 6 months of age and adults, even with co-morbidities such as diabetes, hypertension, suppressed immune systems and pregnant and nursing females; and its exceptional safety profile allows for flexible dosing.

In addition to the beneficial carbon dioxide and saline, as described above, there is further included at least one additional active component. These active components may be any of one or more beneficial additions that are compatible with saline and have some medicinal, curative, pain relieving or moisturizing effect on the sinus cavity walls, vascular system or upper respiratory system. These include, but are not limited to, moisturizers, humectants, over the counter drugs and prescription drugs. Such drugs may be antihistamines, infection treatments, antioxidants, cell growth accelerators, anti-inflammatories, vasoconstrictors, nasal decongestants, or other nasal cavity, wall or upper respiratory treatments. Preferred actives are moisturizers, decongestants, antihistamines, infection treatments and anti-inflammatories. Examples of moisturizers and humectants are: glycerin, propylene glycols (MW 400 to 8000), maltodextrins (liquid), honey, pectin, hydroxypropyl methylcellulose, and carboxymethylcellulose. Examples of topical decongestants are: ephedrine, levomethamphetamine, naphazoline, oxymetazoline, phenylephrine, pseudoephedrine, tramazoline, and xylometazoline. The actives may also be fragrance sensations or fragrance with other benefits, such as eucalyptus, menthol or lavender.

Referring now in detail to the drawings wherein like reference numerals designate corresponding parts throughout the several views, various embodiments of the present invention are shown.

Figure 1:
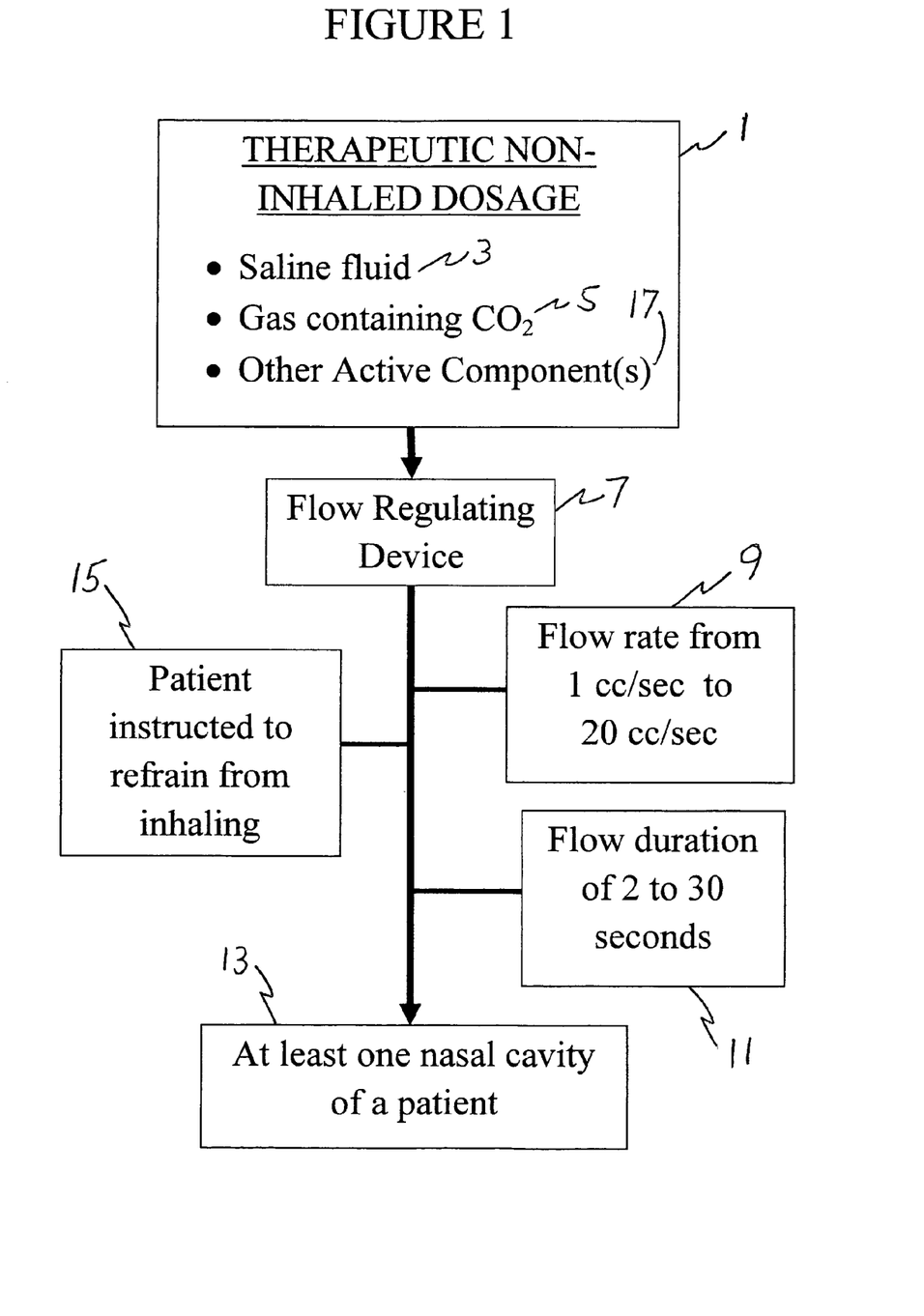
FIG. 1 is a block diagram of an embodiment of the present invention carbon dioxide and saline nasal delivery methods and treatments.

FIG. 1 is a block diagram of an embodiment of the present invention carbon dioxide, saline and additional active component(s) nasal delivery methods and treatments. FIG. 1 illustrates a therapeutic non-inhaled dosage 1 containing saline fluid 3, a carbon dioxide-containing gas 5 and at least one additional active 17. The saline fluid 3 contains water and at least one salt. In some preferred embodiments of the present invention, the salt is sodium chloride. In other embodiments of the present invention, other salts may be used, but it is important that any salt used in the saline fluid 3 must be safe for intranasal use. In some preferred embodiments of the present invention, the concentration of salt in the saline fluid is approximately isotonic with the salt concentration of bodily fluids. In other preferred embodiments, the concentration of salt in the saline fluid is less than the concentration of salt in bodily fluids. In still other preferred embodiments, the concentration of salt in the saline fluid is hypertonic, meaning that it has a salt concentration higher than that of bodily fluids. In still other preferred embodiments, the saline solution is saturated with salt.

The gas 5 contains some portion of carbon dioxide. When the gas 5 containing carbon dioxide is added to the saline fluid 3, the saline fluid 3 becomes carbonated. If the therapeutic non-inhaled dosage 1 containing saline fluid 3 and the gas 5 is kept under pressure, the pressure can later be released (for example by opening a valve), which causes some of the carbon dioxide to bubble out of the solution. This sudden release of carbon dioxide creates effervescence in the therapeutic non-inhaled dosage.

The therapeutic non-inhaled dosage travels through a flow-regulating device 7. In preferred embodiments, the flow-regulating device 7 controls the flow rate 9 of the therapeutic non-inhaled dosage 1 at a rate that is safe and comfortable for the patient. In the embodiment shown in FIG. 1, the flow rate 9 of the therapeutic non-inhaled dosage is between 1 cubic centimeter per second (cc/sec) and 20 cc/sec. In preferred embodiments of the present invention shown in FIG. 1, the flow rate is adjustable to any value between 1 cc/sec and 20 cc/sec.

The therapeutic non-inhaled dosage 1 has a flow duration 11. The flow duration 11 is the length of time during which the therapeutic non-inhaled dosage flows through the flow regulating device into at least one nasal cavity 13 of a patient. In the embodiment shown in FIG. 1, the flow duration 11 is shown as lasting between 2 and 30 seconds. In preferred embodiments of the present invention, the flow duration is adjustable to any value between 2 and 30 seconds.

Figure 2:
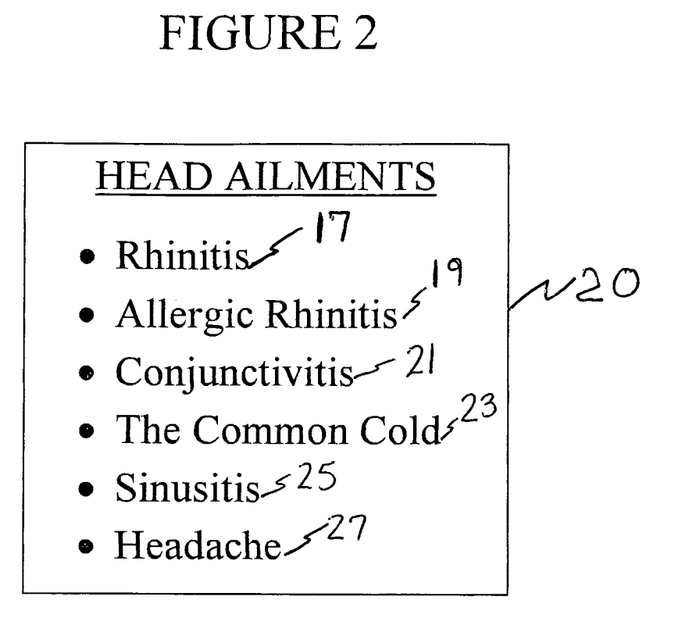
FIG. 2 is a block diagram showing head ailments treated by various embodiments of the present invention carbon dioxide and saline nasal delivery methods and treatments.

After the therapeutic non-inhaled dosage 1 leaves the flow regulating device 7, it enters at least one nasal cavity 13 of a patient. The therapeutic non-inhaled dosage 1 is adsorbed by the nasal tissue and subsequently absorbed by the body. This adsorption and subsequent absorption can have a beneficial effect on many head ailments, some of which are shown in FIG. 2. The effervescent effect of the gas 5 containing carbon dioxide causes better contact between the salt in the saline solution 3 and the nasal tissue.

The additional step 15 of instructing the patient to refrain from inhaling protects the patient from accidently inhaling the therapeutic non-inhaled dosage 1. This is important, even critical, when the therapeutic non-inhaled dosage 1 contains a gas 5 that is substantially 100% carbon dioxide to prevent carbon dioxide poisoning (hypercapnia). Even mild hypercapnia can cause uncomfortable mental and physical effects. Also, when the concentration of salt in the saline solution 3 is greater than isotonic (particularly if salts other than sodium chloride are used), it is desirable to limit the patient's exposure to the salts. The step 15 of instructing the patient not to breathe accomplishes these goals.

Turning now to FIG. 2, a block diagram, block 20, shows some of the medical conditions that can be treated using the present invention carbon dioxide and saline nasal delivery methods and treatments. In some embodiments of the present invention, the carbon dioxide and saline nasal delivery methods and treatments treat rhinitis 17, a swelling of some internal parts of the nose. In other embodiments, the present invention treats allergic rhinitis 19. In still other embodiments, the present invention treats conjunctivitis 21, an inflammation of the conjunctiva also known as pink-eye. In still other embodiments of the present invention, the common cold 23 is treated. In other embodiments of the present invention, sinusitis 25, an inflammation of the sinuses, is treated. In yet other embodiments, the present invention is used to treat headaches 27. It is important to recognize that in some embodiments of the present invention carbon dioxide and saline nasal delivery methods and treatments, multiple conditions can be treated simultaneously. For example, a patient may be suffering from both sinusitis and headache simultaneously; the present invention can alleviate both conditions at the same time. The present invention can treat any ailment shown in FIG. 2 or any combination of those ailments. It should also be recognized that the present invention may be useful in treating other ailments, particularly head ailments. The treatment of other ailments on which the present invention carbon dioxide and saline nasal delivery methods and treatments is effective are considered to be within the scope of the invention.

Figure 3:
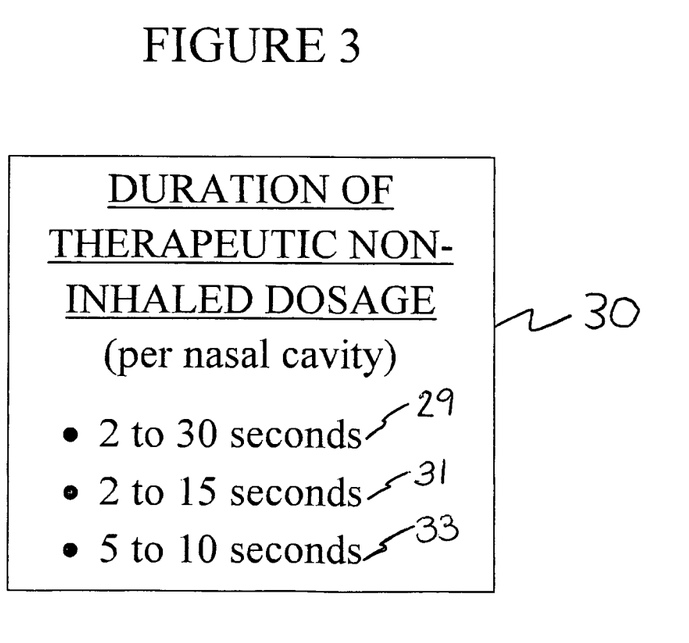
FIG. 3 is a block diagram showing durations for therapeutic non-inhaled dosage in some preferred embodiments of the present invention carbon dioxide and saline nasal delivery methods and treatments.

Turning now to FIG. 3, a block diagram, block 30, shows the durations of therapeutic non-inhaled dosage used in some embodiments of the present invention carbon dioxide and saline nasal delivery methods and treatments. The durations listed in FIG. 3 are ranges, so the actual duration can be any value between the low end of the range and the high end of the range, inclusive. In some embodiments of the present invention, the duration 29 lasts between 2 and 30 seconds. In other embodiments of the present invention, the duration 31 lasts between 2 and 15 seconds. In still other embodiments of the present invention, the duration 33 lasts between 5 and 10 ten seconds. Durations of less than 2 seconds and more than 30 seconds are also considered to be within the scope of the invention.

Figure 4:
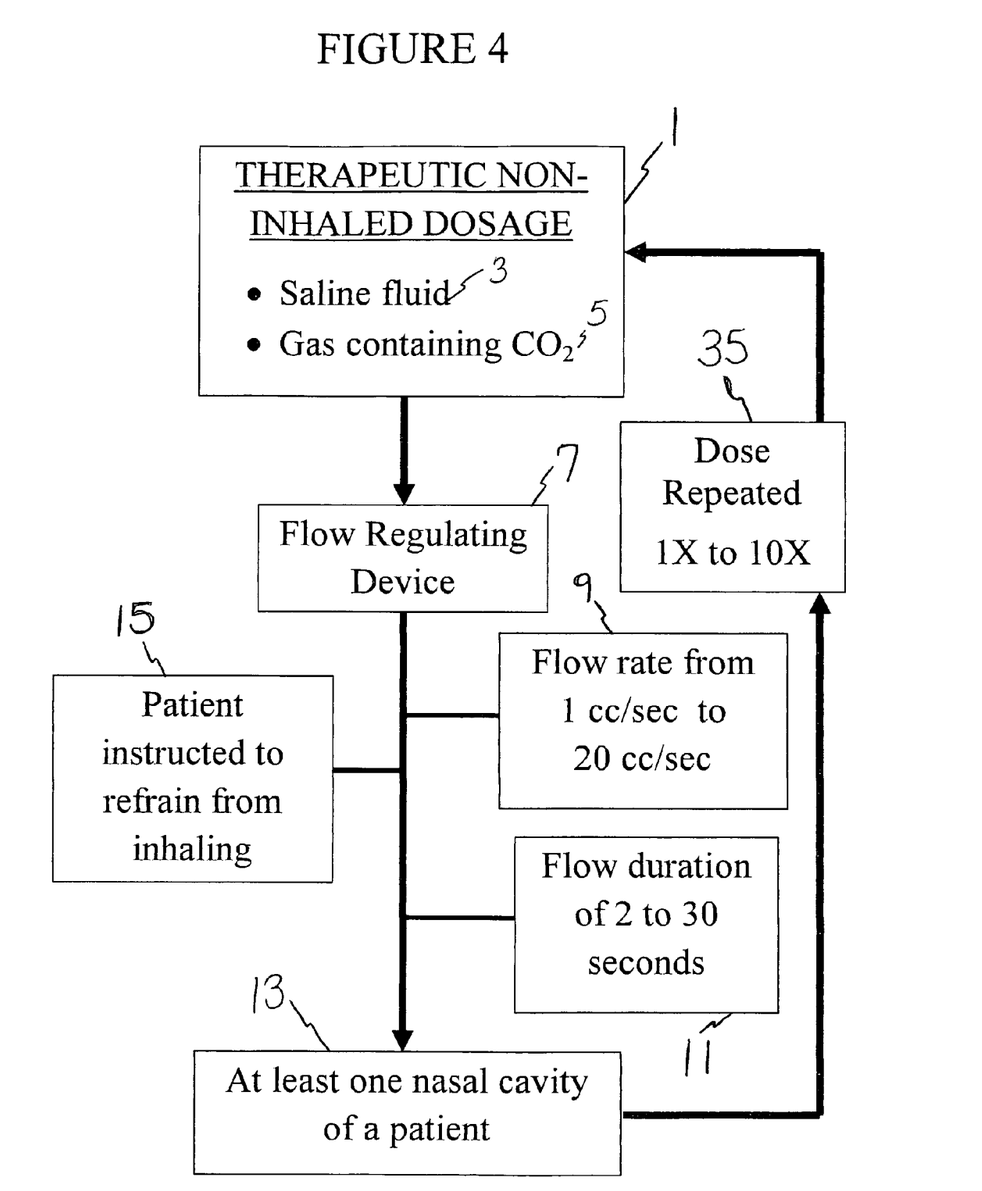
FIG. 4 is a block diagram of another embodiment of the present invention carbon dioxide and saline nasal delivery methods and treatments, showing the additional step of repeating the other steps.

Turning now to FIG. 4, another embodiment of the present invention carbon dioxide and saline nasal delivery methods and treatments is shown. FIG. 4 is a block diagram of an embodiment of the present invention carbon dioxide and saline nasal delivery methods and treatments that incorporates many aspects shown in FIG. 1, and identical blocks are identically numbered. FIG. 4 illustrates a therapeutic non-inhaled dosage 1 containing saline fluid 3 and a gas 5. The saline fluid 3 contains water and at least one salt. In some preferred embodiments of the present invention, the salt is sodium chloride. In other embodiments of the present invention, other salts may be used, but it is important that any salt used in the saline fluid 3 must be safe for intranasal use. In some preferred embodiments of the present invention, the concentration of salt in the saline fluid is approximately isotonic with the salt concentration of bodily fluids. In other preferred embodiments, the concentration of salt in the saline fluid is less than the concentration of salt in bodily fluids. In still other preferred embodiments, the concentration of salt in the saline fluid is hypertonic, meaning that it has a salt concentration higher than that of bodily fluids. In still other preferred embodiments, the saline solution is saturated with salt.

The gas 5 contains some portion of carbon dioxide. When the gas 5 containing carbon dioxide is added to the saline fluid 3, the saline fluid 3 becomes carbonated. If the therapeutic non-inhaled dosage 1 containing saline fluid 3 and the gas 5 is kept under pressure, the pressure can later be released (for example by opening a valve), which causes some of the carbon dioxide to bubble out of the solution. This sudden release of carbon dioxide creates effervescence in the therapeutic non-inhaled dosage.

The therapeutic non-inhaled dosage travels through a flow-regulating device 7. In preferred embodiments, the flow-regulating device 7 controls the flow rate 9 of the therapeutic non-inhaled dosage 1 at a rate that is safe and comfortable for the patient. In the embodiment shown in FIG. 1, the flow rate 9 of the therapeutic non-inhaled dosage is between 1 cubic centimeter per second (cc/sec) and 20 cc/sec. In preferred embodiments of the present invention shown in FIG. 1, the flow rate is adjustable to any value between 1 cc/sec and 20 cc/sec.

The therapeutic non-inhaled dosage 1 has a flow duration 11. The flow duration 11 is the length of time during which the therapeutic non-inhaled dosage flows through the flow regulating device into at least one nasal cavity 13 of a patient. In the embodiment shown in FIG. 1, the flow duration 11 is shown as lasting between 2 and 30 seconds. In preferred embodiments of the present invention, the flow duration is adjustable to any value between 2 and 30 seconds.

After the therapeutic non-inhaled dosage 1 leaves the flow regulating device 7, it enters at least one nasal cavity 13 of a patient. The therapeutic non-inhaled dosage 1 is adsorbed by the nasal tissue. This adsorption can have a beneficial effect on many head ailments, some of which are shown in FIG. 2. The effervescent effect of the gas 5 containing carbon dioxide causes better contact between the salt in the saline solution 3 and the nasal tissue.

The additional step 15 of instructing the patient to refrain from inhaling protects the patient from accidently inhaling the therapeutic non-inhaled dosage 1. This is important, even critical, when the therapeutic non-inhaled dosage 1 contains a gas 5 that is substantially 100% carbon dioxide to prevent carbon dioxide poisoning (hypercapnia). Even mild hypercapnia can cause uncomfortable mental and physical effects. Also, when the concentration of salt in the saline solution 3 is greater than isotonic (particularly if salts other than sodium chloride are used), it is desirable to limit the patient's exposure to the salts. The step 15 of instructing the patient not to breathe accomplishes these goals.

In the embodiment shown in FIG. 4, after the therapeutic non-inhaled dosage 1 passes through the flow regulating device 7 and into the at least one nasal cavity 13 of a patient, the dose is repeated 35. In some preferred embodiments, the dose is repeated 35 between one and ten times. In still other embodiments, the dose is repeated more than ten times. The step 35 of repeating the dose can be used if a single application of the therapeutic non-inhaled dosage 1 is insufficient to alleviate the head ailment or ailments from which the patient suffers.

Figure 5:
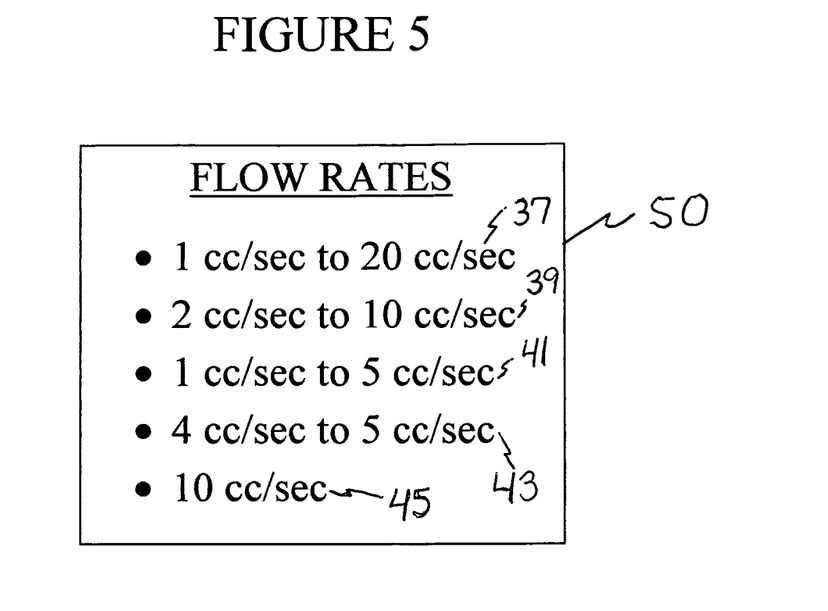
FIG. 5 is a block diagram showing flow rates in some preferred embodiments of the present invention carbon dioxide and saline nasal delivery methods and treatments.

Turning now to FIG. 5, a block diagram, block 50, shows flow rates used in some embodiments of the present invention carbon dioxide and saline nasal delivery methods and treatments. The flow rates used in FIG. 5 are shown as ranges, and the actual rate of the flow may any value between the low end of the range and the high end of the range, inclusive. In some embodiments, a rate 37 between 1 cc/sec and 20 cc/sec is used. In other embodiments, a flow rate 39 between 2 cc/sec and 10 cc/sec is used. In other preferred embodiments, a flow rate 41 between 1 cc/sec and 5 cc/sec is used. In still other preferred embodiments, a flow rate 43 between 4 cc/sec and 5 cc/sec is used. In still other preferred embodiments, a flow rate 45 of approximately 10 cc/sec is used. Embodiments with flow rates of less than 1 cc/sec or more than 20 cc/sec are also considered to be within the scope of the invention.

Figure 6:
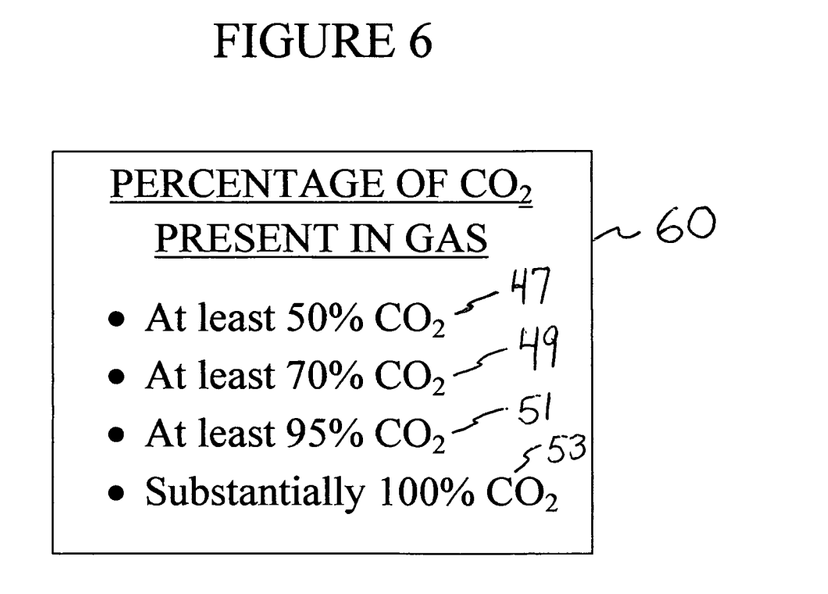
FIG. 6 is a block diagram showing the percentage of carbon dioxide present in the gas in some additional preferred embodiments of the present invention carbon dioxide and saline nasal delivery methods and treatments; and, FIG. 7 illustrates a block diagram showing monodose and multidose dispensers that may be used in the present invention methods.

Turning now to FIG. 6, a block diagram, block 60, shows levels of carbon dioxide in the gases used in some embodiments of the present invention. The levels of carbon dioxide are expressed as a percentage of the gas (3 in FIGS. 1 and 4) used in the therapeutic non-inhaled dosage (1 in FIGS. 1 and 4). In some embodiments of the present invention carbon dioxide and saline nasal delivery methods and treatments, the amount of carbon dioxide 47 in the gas is at least 50%. In other embodiments, the amount of carbon dioxide 49 in the gas is at least 70%. In still other embodiments, the amount of carbon dioxide 51 in the gas is at least 95%. In other preferred embodiments, the amount of carbon dioxide 53 in the gas is substantially 100%. Gases with a percent composition of less than 50% carbon dioxide are also considered to be within the scope of the invention.

Figure 7:
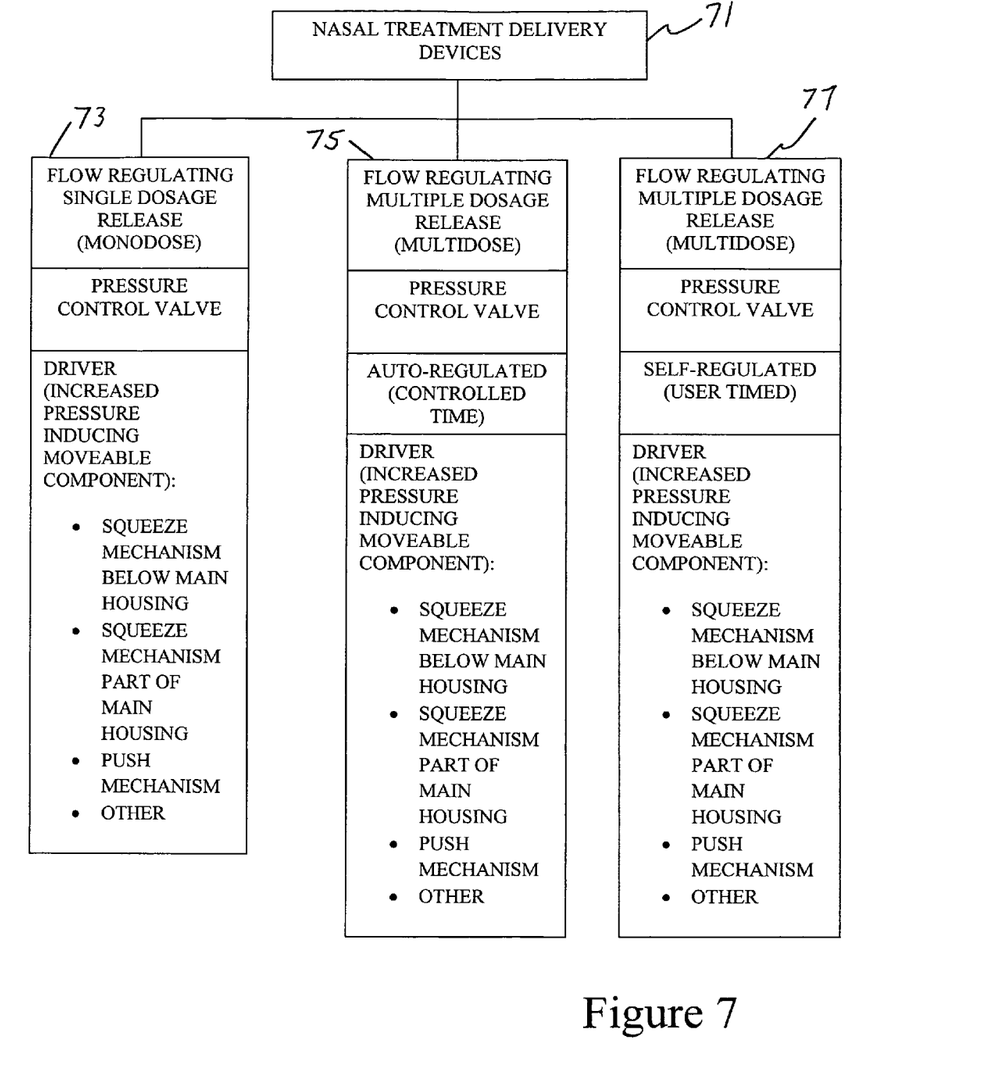

FIG. 7 illustrates a block diagram showing monodose and multidose dispensers that may be used in the present invention methods. Here, block 71 illustrates the caption of the Figure, namely, flow regulating devices. Block 73 shows that the flow regulating device used in the present invention methods may be a single dose dispenser (monodose) with a pressure control valve for flow rate regulation. The rate of flow is set in accordance with the ranges set forth above. In the case of a monodose dispenser, the entire dose is dispensed, so that time of dispensing does not need to be controlled—it is just the time it takes to unload the dose. Thus, a monodose dispenser may controllably release a pressurized mixture of the carbon dioxide and the saline, until it stops flowing.

On the other hand, a plural or multidose dispenser may be used, and needs dispensing on/off control, otherwise the entire contents could be unnecessarily released in one shot. Thus, block 75 illustrates the use of a multidose dispenser with a pressure control valve for flow rate regulation. The rate of flow is set in accordance with the ranges set forth above. Block 77 shows one multidose dispenser option wherein the user controls the release time, so that there is variable dosage. For example, there may be an activator, such as a push button or a squeeze mechanism to release the dosage, and the user may be directed to dispense for a time, e.g., dispense for eight to ten seconds. Alternatively, as shown in block 79, an auto-controlled release mechanism may be used, e.g., a spring return release that closes a valve based on set timing, or a dual spring device with one being reverse spring mechanism that returns a lever to control the time of release. Timed valving is well known in the field of medicine dispensing and any available multidose fixed time dispensing mechanism may be utilized.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims.

What is claimed is:

1. A method for treating head ailments in a patient in need thereof, said method, comprising:
    directing a therapeutic, non-inhaled dosage to at least one nasal cavity of said patient through a flow regulating device, said dosage including: a) a saline fluid, b) a gas containing carbon dioxide and c) at least one additional active component, wherein the therapeutic, non-inhaled dosage is delivered at a flow rate from 1 cc/sec to 5 cc/sec for a duration of 2 to 30 seconds, while said patient is substantially refraining from inhaling and wherein said gaseous carbon dioxide is dissolved in said saline fluid and said at least one additional active component, wherein a pressure-charging moveable component is located on said flow regulating device and wherein the dose may be repeated from 1 to 10 times.

2. The method of claim 1, wherein said treated head ailment is selected from the group consisting of rhinitis, conjunctivitis, common cold and sinusitis.

3. The method of claim 1, wherein said method is treating rhinitis and the rhinitis is allergic rhinitis.

4. The method of claim 1, wherein said method is treating conjunctivitis.

5. The method of claim 1, wherein said method is treating sinusitis.

6. The method of claim 1, wherein said method is treating common cold.

7. The method of claim 1, wherein said head ailment is headache.

8. The method of claim 1, wherein said flow regulating device is a single dose dispenser with a pressure control for released flow regulation.

9. The method of claim 1, wherein said flow regulating device is a multiple dose dispenser with a pressure control for released flow regulation.

10. The method of claim 9, wherein said multiple dose dispenser furthers a dosage amount control mechanism and activator to limit dosage release amount for each activation.

11. The method of claim 1, wherein the duration is 5 to 10 seconds per nasal cavity.

12. The method of claim 1, wherein the duration is 2 to 15 seconds per nasal cavity.

13. The method of claim 1, wherein the flow rate is from 2 cc/sec to 5 cc/sec.

14. The method of claim 1, wherein the flow rate is from 4 cc/sec to 5 cc/sec.

15. The method of claim 1 wherein the gas comprises at least 50% carbon dioxide.

16. The method of claim 1 wherein the gas comprises at least 70% carbon dioxide.

17. The method of claim 1 wherein the gas comprises substantially pure carbon dioxide.

* * * * *